(12) United States Patent
Batich et al.

(10) Patent No.: US 7,045,673 B1
(45) Date of Patent: *May 16, 2006

(54) INTRINSICALLY BACTERICIDAL ABSORBENT DRESSING AND METHOD OF FABRICATION

(75) Inventors: Christopher D. Batich, Gainesville, FL (US); Bruce A Mast, Gainesville, FL (US); Gregory Schultz, Gainesville, FL (US); Gerald M. Olderman, New Bedford, MA (US); David S. Lerner, Boca Raton, FL (US)

(73) Assignees: Quick-Med Technologies, Inc., Gainesville, FL (US); University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/857,906

(22) PCT Filed: Dec. 8, 1999

(86) PCT No.: PCT/US99/29091

§ 371 (c)(1),
(2), (4) Date: Jan. 4, 2002

(87) PCT Pub. No.: WO00/33778

PCT Pub. Date: Jun. 15, 2000

Related U.S. Application Data

(60) Provisional application No. 60/111,472, filed on Dec. 9, 1998.

(51) Int. Cl.
A61F 13/00 (2006.01)

(52) U.S. Cl. .................. 602/48; 602/42; 602/43; 424/443; 424/447

(58) Field of Classification Search ............ 602/41–59; 424/441–449; 604/304–308; 128/888, 889
See application file for complete search history.

(56) References Cited

U.S. PATENT DOCUMENTS

| | | | |
|---|---|---|---|
| 3,490,454 A | 1/1970 | Goldfarb et al. | |
| 3,563,243 A | 2/1971 | Lindquist | |
| 3,691,271 A | 9/1972 | Charle et al. | |
| 3,778,476 A | 12/1973 | Rembaum et al. | |
| 3,874,870 A | 4/1975 | Green et al. | |
| 3,898,336 A | 8/1975 | Rembaum et al. | |
| 3,931,319 A | 1/1976 | Green et al. | |
| 3,945,842 A | 3/1976 | Green | |
| 4,013,507 A | 3/1977 | Rembaum | |
| 4,027,020 A | 5/1977 | Green et al. | |
| 4,076,663 A | 2/1978 | Masuda et al. | |
| 4,089,977 A | 5/1978 | Green et al. | |
| 4,111,679 A | 9/1978 | Shair et al. | |
| 4,191,743 A | 3/1980 | Klemm et al. | |
| 4,226,232 A | 10/1980 | Spence | |
| 4,393,048 A | 7/1983 | Mason et al. | |
| 4,506,081 A | 3/1985 | Fenyes et al. | |
| 4,563,184 A | 1/1986 | Korol | |
| 4,570,629 A | 2/1986 | Widra | |
| 4,581,058 A | 4/1986 | Fenyes et al. | |
| 4,657,006 A | 4/1987 | Rawlings et al. | |
| 4,728,323 A | 3/1988 | Matson | |
| 4,778,813 A | 10/1988 | Fenyes et al. | |
| 4,791,063 A | 12/1988 | Hou et al. | |
| 4,810,567 A | 3/1989 | Calcaterra et al. | |
| 4,878,908 A * | 11/1989 | Martin et al. .................. 623/1 |
| 4,902,565 A | 2/1990 | Brook | |
| 4,904,247 A | 2/1990 | Therriault et al. | |
| 4,929,498 A | 5/1990 | Suskind et al. | |
| 4,960,590 A | 10/1990 | Hollis et al. | |
| 4,970,211 A | 11/1990 | Fenyes et al. | |
| 5,035,892 A * | 7/1991 | Blank et al. .................. 424/443 |
| 5,045,322 A | 9/1991 | Blank et al. | |
| 5,051,124 A | 9/1991 | Pera | |
| 5,056,510 A | 10/1991 | Gilman | |
| 5,069,907 A | 12/1991 | Mixon et al. | |
| 5,091,102 A | 2/1992 | Sheridan | |
| 5,093,078 A | 3/1992 | Hollis et al. | |
| 5,106,362 A | 4/1992 | Gilman | |
| 5,147,338 A | 9/1992 | Lang et al. | |
| 5,236,703 A | 8/1993 | Usala | |
| 5,295,978 A | 3/1994 | Fan et al. | |
| 5,302,392 A | 4/1994 | Karakelle et al. | |
| 5,429,628 A * | 7/1995 | Trinh et al. .................. 604/359 |

(Continued)

FOREIGN PATENT DOCUMENTS

WO  WO 99/32157 A2  7/1999

OTHER PUBLICATIONS

Butler, G., "Cyclopolymerization and Cyclocopolymerization", (book), 1992, pp. 246 & 272, footnote 35, Marcel Dekker, Inc., New York.*

(Continued)

*Primary Examiner*—Kim M. Lewis
(74) *Attorney, Agent, or Firm*—Gerry J. Elman; Elman Technology Law P.C.

(57) ABSTRACT

Absorbent dressings, including highly-absorbent dressings having antimicrobial polymer attached thereto via non-siloxane bonds are disclosed. Bandages (i.e. wound dressing), sanitary napkins and the like are useful applications for the intrinsically bactericidal absorbent dressings whose method of manufacture and use are disclosed and claimed.

13 Claims, No Drawings

U.S. PATENT DOCUMENTS

| | | | |
|---|---|---|---|
| 5,432,000 | A | 7/1995 | Young, Sr. et al. |
| 5,441,742 | A | 8/1995 | Autant et al. |
| 5,498,478 | A | 3/1996 | Hansen et al. |
| H1575 | H | 8/1996 | Daugherty et al. |
| 5,580,974 | A | 12/1996 | Banker et al. |
| 5,641,503 | A | 6/1997 | Brown-Skrobot |
| 5,662,913 | A | 9/1997 | Capelli |
| 5,670,557 | A | 9/1997 | Dietz et al. |
| 5,672,418 | A * | 9/1997 | Hansen et al. ............... 428/283 |
| 5,674,346 | A | 10/1997 | Kundel |
| 5,674,561 | A | 10/1997 | Dietz et al. |
| 5,695,456 | A | 12/1997 | Cartmell et al. |
| 5,719,201 | A | 2/1998 | Wilson |
| H1732 | H | 6/1998 | Johnson |
| 5,782,787 | A | 7/1998 | Webster |
| 5,811,471 | A | 9/1998 | Shanbrom |
| 5,830,526 | A | 11/1998 | Wilson et al. |
| 5,856,248 | A | 1/1999 | Weinberg |
| 5,985,301 | A | 11/1999 | Nakamura et al. |
| 6,030,632 | A | 2/2000 | Sawan et al. |
| 6,039,940 | A | 3/2000 | Perrault et al. |
| 6,126,931 | A | 10/2000 | Sawan et al. |
| 6,146,688 | A | 11/2000 | Morgan et al. |
| 6,160,196 | A | 12/2000 | Knieler et al. |
| 6,316,044 | B1 | 11/2001 | Ottersbach et al. |
| 2002/0177828 | A1* | 11/2002 | Batich et al ................ 604/367 |

OTHER PUBLICATIONS

Shkunikova, I.S., "Izv Akad Nauk Sssr", 1984; 4: 928-9, publication provided.*

Butler, G., "Cyclopolymerization and Cyclocopolymerization", (book), 1992, pp. 246 & 272, footnote 35, Marcel Dekker, Inc., New York.

Shkunikova, I.S., "Izv Akad Nauk Sssr", 1984; 4:928-9, publication provided.

Tweden et al. "Silver Modification of Polyethylene Terephthalate Textiles for Antimicrobial Protection"; ASAIO Journal, 43, pM475-M481 (1997).

Donaruma, L. G. , et al. ,"Anionic Polymeric Drugs", John Wiley & Son, New York, (1978); Ikeda T, Yamaguchi H, and Tazuke, S"New Polymeric Biocides: Synthesis and Antibacterial Activities of Polycations with Pendant Biguanide Groups" ; Antimicrob. Agents Chemother. 26 (2), p. 139-44 (1984).

G. Mino and S. Kaizerman;"A New Method for the Preparation of Graft Copolymers. Polymerization Initiated by Ceric Ion Redox Systems", Journal of Polymer Science 31 (122), p. 242 (1958).

S. B. Vitta, et al. ,"The Preparation and Properties of Acrylic and Methacrylic Acid Grafted Cellulose Prepared by Ceric Ion Initiation. Part I. Preparation of the Grafted Cellulose", J. Macromolecular Science-Chemistry A22 (5-7) p. 579-590 (1985).

M. Mishra, Graft Copolymerization of Vinyl Monomers onto Silk Fibers, J. Macromolecular Science, Reviews in Macromolecular Chemistry C19 (2), PI 93-220 (1980).

Ikeda, T. "Antibacterial Activity of Polycationic Biocides", Chapter 42, p. 743 in: High Performance Biomaterials, M. Szycher, ed. , Technomic, Lancaster PA, (1991).

Yahiaoui, A. "Covalent Attachment of Hydrophilic Groups Onto the Surface of LowDensity Polyethylene," Master's Thesis, University of Florida, 1986.

Stannett, Vivian T, "Cellulose Grafting: Past, Present, and Future," Polymers from Biobased Materials, 1989 , p. 58-69, Chapter 3, William Andrews Publishing, Norwich, NY.

Broughton et al., "Textiles Having the Ability to Deliver Reactive Chemical Systems". National Textile Center Annual Report, Nov. 1999, p. 1-6.

* cited by examiner

INTRINSICALLY BACTERICIDAL ABSORBENT DRESSING AND METHOD OF FABRICATION

Application 09/857,906 filed Jan. 4, 2002 the National Stage entry of PCT/US99/29091 filed Dec. 8, 1999 which claims priority to Provisional 60/111,472 filed Dec. 9, 1998.

FIELD OF THE INVENTION

This invention relates generally to absorbent dressings, and more particularly highly-absorbent synthetic polymer dressings having antimicrobial agents attached thereto.

BACKGROUND OF THE INVENTION

Bacterial growth in absorbent dressings for wounds, urinary incontinence diapers, and menstruation pads can lead to serious medical complications as well as social difficulties. For example, bacterial growth in urinary incontinence diapers or menstruation pads usually produces among, unpleasant odors that are socially unacceptable and can cause persons to alter their lifestyle. Conventional absorbent pads for urinary incontinence and menstruation are not inherently bactericidal. Consequently, the only way to avoid growth of bacteria in the absorbent dressings is to change them at frequent intervals, even if the absorbent capacity of the pad has not been reached. In the area of wound dressings, bacterial contamination of acute wounds and infection of chronic skin wounds are major clinical problems that can result in significant morbidity and, in severe cases, mortality. Conventionally, wound dressings have been designed to absorb wound fluids and yet provide a moist environment for promoting wound healing. However, such moist environments create a nutrient rich reservoir for bacterial growth in the dressing. Bacteria growing in the dressing can be shed back into the wound, increasing the risk of wound infection, or response to toxins, and producing strong, foul odors.

In an effort to address these problems, antibiotics or chemical disinfectants are frequently applied topically to wounds prior to covering the wound with a dressing. Alternatively, topical agents are sometimes applied directly to the surface of the dressing. To control foul odors, some known dressings incorporate charcoal powder to absorb molecules generating the foul odor. For some applications, topical application of antibacterial agents is not desirable. For instance, bactericidal agents applied topically to wound dressings have a tendency to seep into the wound being treated. Furthermore, many antimicrobial drugs, such as iodine, are cytotoxic and will retard wound healing if used repetitively or at high concentrations.

A composition comprising a superabsorbent polymer having a monolayer (or near monolayer) of silane antimicrobial agent in a covalent bonding relationship with the base polymer is disclosed in U.S. Pat. No. 5,045,322. The composition may be in the form of flakes, strips, powders, filaments, fibers or films, and may be applied to a substrate in the form of a coating. The aforementioned composition is less apt to enter a wound vis-a-vis conventional topical treatment systems. In that respect, the disclosed composition provides an improvement over conventional topical treatment systems. However, silanes contain siloxane bonds which can be cleaved by acids and bases produced by infection or bacterial growth. In turn, these reactions may weaken or destroy bends between the silane antimicrobial agent and the underlying polymer. Consequently, antimicrobial agent may seep into a wound and retard wound healing.

The need exists for an improved antimicrobial dressing composition having an antimicrobial agent which can be maintained securely attached to a superabsorbent polymer upon exposure to acids and bases produced by infection and bacterial growth. In addition to reducing the propensity for detachment of the antimicrobial agent, it would be desirable to provide a surface area enhanced dressing structure for increasing the effectiveness of the antimicrobial agent.

SUMMARY OF THE INVENTION

It is an object of the present invention to provide an inherently bactericidal superabsorbant dressing having an enhanced surface area.

It is another object of the present invention to provide an inherently bactericidal superabsorbant dressing having an improved bactericidal attachment structure that resists degradation upon exposure to acids or bases produced, for instance, during bacterial growth.

These and other objects are achieved by the inherently bactericidal polymer composition and the present invention. In the preferred embodiment, the composition comprises a polymer matrix having quaternary ammonium groups tethered to its surface through non-siloxane bonds. The surface area of the polymer matrix is enhanced, for instance, by electrostatically spinning a fiber-forming synthetic polymer to form a frayed fiber or filament. Alternatively, the polymer solution can be wet- or dry-spun to create a roughened fiber surface by controlling the choice of solvent and the polymer solution temperature. Additional surface area enhancement is provided by tethering molecular chains of quaternary ammonium pendent groups to the surface of the polymer matrix. Tethering may be accomplished by known techniques such as grafting and selective adsorption.

In an alternate embodiment of the invention, non-ionic bactericidal molecules are coupled to the surface of the polymer matrix, in lieu of ionically-charged molecules. Ionically-charged molecules are prone to being neutralized upon encountering oppositely-charged molecules. For instance, positively-charged quaternary ammonium groups may be neutralized by negatively-charged chloride ions present in physiological fluids. In instances were such neutralization is significant enough to reduce the bactericidal properties of the dressing below an acceptable level, non-ionic surface groups may be preferable.

DETAILED DESCRIPTION OF THE PREFERRED EMBODIMENTS

A novel antibacterial polymer composition is fabricated to have an enhanced surface area and superabsorbent capacity for biological fluids, including urine, blood, and wound exudate.

In the preferred embodiment of the present invention, the composition includes a polymer matrix having quaternary ammonium compounds attached to the surface of the polymer matrix. The polymer matrix is comprised of a plurality of hydrophilic fibers or filaments which can be fabricated in any suitable manner. For example, suitable fibers or filaments can be fabricated by wet- or dry-spinning a fiber-forming synthetic polymer from a spinning solvent. The resulting polymer has superabsorbent capacity. Generally, polymers capable of absorbing from about thirty to sixty grams of water per gram of polymer are considered to be superabsorbent. Examples of superabsorbent polymers which can be fabricated in this manner include polyacrylic acids, polyethylene oxides and polyvinyl alcohols. For example, methods for spinning polyethylene oxide using acetone solvent are well known.

Significantly, the polymer matrix is fabricated to have an enhanced surface area. Enhancing the surface area of the polymer matrix results in improved absorption of biological fluids, and increases the availability of sites for attachment of the antimicrobial quaternary ammonium compounds. A corresponding increase in the quantity and density of antimicrobial sites, in turn, enhances the efficacy of the composition in killing organisms such as bacteria and viruses.

It may occur to one skilled in the art of polymer science that a variety of methods are available for accomplishing surface area modification. Preferably, surface area enhancement is accomplished by a modified spinning or casting method. For instance, electrostatic spinning is a modified spinning technique which results in fraying of the fiber as it exits the spinerette. Alternatively, a polymer solution can be wet- or dry-spun to create a roughened fiber surface by controlling the solvent type and the polymer solution temperature. This technology is well known and has been applied, for example, in the manufacture of asymmetric membranes having roughened pores for dialysis. The size of the roughened pores is primarily controlled by the speed of precipitation which, in turn, is controlled by solvent interaction parameters, temperature, etc.

The surface area of the polymer composition is further enhanced by tethering chains of antimicrobial groups to the outer surface of the individual polymer fibers. Preferably, molecular chains of quaternary ammonium pendent groups are fabricated to have at least one end adapted for attachment to a fiber surface. For instance, surface grafting may be accomplished by creating surface free radicals as initiation sites from peroxide generation (ozone or microwave). Alternatively, surface attachment of an interpenetrating network may be achieved using a monomer which swells the substrate polymer. The incorporation of tethered antimicrobial chains has the further benefit of enhancing the functionality of the composition. In particular, the tethered antimicrobial chains extend into the particular biological solution to bind to harmful bacterial and viral organisms. In contrast to known dressing compositions in which a monolayer (or near monolayer) of bactericidal compound is directly attached to a fiber surface, the chain structures of the present invention, which function like arms extending outwardly from the fiber surface, more effectively bind the antimicrobial sites to harmful organisms. Preferably, tethering is accomplished by grafting the antimicrobial chains directly to the matrix surface, or by selective adsorption of a copolymer to the matrix surface.

Grafting techniques are well known in the art. For example, quaternary ammonium compound grafting using the monomer trimethylammonium ethyl methacrylate to graft polymerize to a modified polyethylene surface is described by Yahaioui (Master's Thesis, University of Florida, 1986). Yahioui describes a grafting technique in which a plasma discharge is used to create free radicals which initiate polymerization of appropriate monomers. Selective adsorption of appropriate block copolymers can also be used.

In contrast to known compositions in which an antimicrobial structure is achieved by covalently bonding silane groups to the surface of the base polymer, the present invention incorporates a chemical structure which is based on polymerization (i.e., surface grafting) of monomers containing all carbon-carbon, carbon-oxygen and carbon-nitrogen main bonds, such as the dialkly, diallyl, quaternary ammonium compounds. Consequently, the composition of the present invention results in a structure which is less prone to reacting with acids and bases produced by bacterial growth. As previously mentioned, such reactions can degrade the attachment between the matrix and antimicrobial groups. In instances where the composition is applied to a wound dressing, such degradation could result in antimicrobial agents detaching from the polymer matrix and entering a wound site. In some cases, this can have the deleterious effect of retarding wound healing.

In an alternate embodiment of the present invention, anionic antibactericidal groups are immobilized on the surface of a superabsorbant dressing to improve the antibactericidal efficacy of the dressing. The positive charge associated with quaternary ammonium groups, for example, can be neutralized by negative ions, such as chloride ions present in physiological fluids such as urine and plasma. For applications where the degree of neutralization will significantly reduce the effectiveness of the antibactericidal agent, anionic surface groups can be substituted for quaternary ammonium groups. Examples of chemical compounds that can be used to produce immobilized anionic surface groups include Triton-100, Tween 20 and deoxycholate. For instance, Triton-100 contains a free hydroxyl group which can be derivatized into a good leaving group, such as tosyl or chloride, and subsequently reacted with a base-treated polymer, such as methyl cellulose, to yield a surface immobilized non-ionic surfactant.

Dimethyldiallyl ammonium chloride is one example of a suitable monomer which may be used with the present invention. This monomer, commonly referred to as DMDAC or DADMAC, is used in the fabrication of commercial flocculating polymers. Modifications of trialkyl(p-vinylbenzyl) ammonium chloride or the p-trialkylaminoethyl styrene monomers are also suitable. One such example is trimethyl (p-vinyl benzyl) ammonium chloride; the methyl groups of this monomer can be replaced by other alkyl groups to impart desired properties. Alternatively, methacrylate-based monomers may be used; however, they may suffer from hydrolytic instability under acidic and basic conditions in a fashion similar to the silane-based treatments of the prior art. Consequently, methacrylate-based monomers are not preferred.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. An intrinsically antimicrobial material comprising:
   an absorbent polymeric matrix having an enhanced surface area;
   wherein said enhanced surface area further comprises a polymer of antimicrobial monomeric moieties attached to said matrix via non-siloxane covalent chemical bonds so as to result in a structure which is less prone to degradation by acids or bases produced during bacterial growth and consequent detachment of said polymer of antimicrobial monomeric moieties from the matrix, whereby the material remains antimicrobial after exposure of the material to skin or aqueous biological fluids.

2. The material of claim 1, wherein said aqueous biological fluids are bodily fluids, sweat, tears, mucus, urine, menses, blood, wound exudates, or mixtures thereof.

3. The material of claim 1, wherein molecules of said polymer are attached to said matrix via one or more covalent carbon-oxygen-carbon bonds, or carbon-carbon bonds, or carbon-nitrogen bonds, or combinations thereof.

4. The material of claim 1, wherein said antimicrobial monomeric moieties are allyl- or vinyl-containing monomers.

5. The material of claim 1, wherein said antimicrobial monomeric moieties comprise at least one quaternary ammonium compound.

6. The material of claim 5, wherein the quaternary ammonium compound is dimethyldiallyl ammonium chloride, or a trialkyl(p-vinylbenzyl)ammonium chloride, or a p-trialkylaminoethyl styrene monomer.

7. The material of claim 1, wherein said matrix comprises cellulose.

8. The material of claim 1, wherein said matrix comprises a polyethylene oxide, a polyvinyl alcohol, or a polyacrylate.

9. The material of claim 1, wherein said matrix consists essentially of hydrophilic fibers or filaments having a superabsorbent capacity for aqueous biological fluids as evidenced by being capable of absorbing at least about thirty times its own weight of water.

10. An absorbent dressing, diaper, sanitary pad, or tampon comprising the intrinsically antimicrobial material of claim 1.

11. A method for fabricating the intrinsically antimicrobial material of claim 9 comprising the steps of:
    forming an absorbent polymeric matrix having an enhanced surface area; and
    attaching a polymer of antimicrobial monomeric moieties in an amount sufficient to impart to the material an antimicrobial effect which remains after exposure of the material to skin or aqueous biological fluids.

12. The method of claim 11, wherein said antimicrobial monomeric moieties comprise at least one quaternary ammonium compound.

13. The method of claim 12, wherein the quaternary ammonium compound is dimethyldiallyl ammonium chloride, or a trialkyl(p-vinylbenzyl)ammonium chloride, or a p-trialkylaminoethyl styrene monomer.

* * * * *

UNITED STATES PATENT AND TRADEMARK OFFICE
CERTIFICATE OF CORRECTION

PATENT NO. : 7,045,673 B1
APPLICATION NO. : 09/857906
DATED : May 16, 2006
INVENTOR(S) : Christopher D. Batich et al.

It is certified that error appears in the above-identified patent and that said Letters Patent is hereby corrected as shown below:

Column 6, Line 5: "9" should read -- 1 --

Signed and Sealed this

Nineteenth Day of December, 2006

JON W. DUDAS
*Director of the United States Patent and Trademark Office*